(12) United States Patent
Nazareth et al.

(10) Patent No.: US 8,211,711 B2
(45) Date of Patent: Jul. 3, 2012

(54) DIAGNOSTIC DETECTION DEVICE

(75) Inventors: Albert Nazareth, Mercerville, NJ (US);
Timothy Snowden, Howell, NJ (US);
Yea-shun Cheng, Doylestown, PA (US)

(73) Assignee: Church & Dwight Co., Inc., Princeton, NJ (US)

( * ) Notice: Subject to any disclaimer, the term of this patent is extended or adjusted under 35 U.S.C. 154(b) by 203 days.

(21) Appl. No.: 12/823,949

(22) Filed: Jun. 25, 2010

(65) Prior Publication Data

US 2010/0261293 A1 Oct. 14, 2010

Related U.S. Application Data

(62) Division of application No. 11/681,061, filed on Mar. 1, 2007, now Pat. No. 7,776,618.

(51) Int. Cl.
*G01N 33/558* (2006.01)

(52) U.S. Cl. ........ 436/514; 422/401; 422/420; 422/425; 435/7.5; 435/287.2; 435/287.7; 435/287.9; 435/805; 435/810; 435/970; 436/518; 436/524; 436/525; 436/810

(58) Field of Classification Search .................. None
See application file for complete search history.

(56) References Cited

U.S. PATENT DOCUMENTS

| | | |
|---|---|---|
| 4,313,734 A | 2/1982 | Leuvering |
| 4,366,241 A | 12/1982 | Tom et al. |
| 5,739,041 A | 4/1998 | Nazareth et al. |
| 5,846,835 A | 12/1998 | Sisbarro et al. |
| 6,319,676 B1 | 11/2001 | Nazareth et al. |
| 6,485,982 B1 | 11/2002 | Charlton |
| 7,045,342 B2 | 5/2006 | Nazareth et al. |

OTHER PUBLICATIONS

Frens, "Controlled Nucleation for the Regulation of the Paraticle Size in Monodisperse Gold Suspensions," *Nature, Physical Science*, 1973, pp. 20-22, vol. 241.

Horisberger, Evaluation of Colloidal Gold as a Cytochemical Marker for Transmission and Scanning Electron Microscope, *Bio. Cellulaire*, 1979, pp. 253-258, vol. 36.

Leuvering et al., "Sol Particle Immunoassay," *J. Immunoassay*, 1980, pp. 77-91, vol. 1, No. 1.

Tijssen, "Practice and Theory of Enzyme immunoassays The Immunoreactants on Solid Phases", *Laboratory Techniques in Biochemistry and Molecular Biology*, Chapter 13, pp. 297-328, vol. 15, 1985.

*Primary Examiner* — Chris L Chin
(74) *Attorney, Agent, or Firm* — Ryan W. Cagle; Stephen B. Shear

(57) ABSTRACT

The invention comprises a device for detecting an analyte in a liquid sample deposited on a first portion of the device for transport to a second portion of the device that is in fluid contact with the first portion. In specific embodiments, the device comprises a labeled conjugate comprising a binding member reactive with a first epitope of the analyte and a label comprising a gold colloid, preferably having a mean particle size of 50 nm to 100 nm. In further embodiments, the device comprises a capture component comprising polymerized streptavidin. The diagnostic device is particularly useful in the preparation of pregnancy test kits.

18 Claims, 7 Drawing Sheets

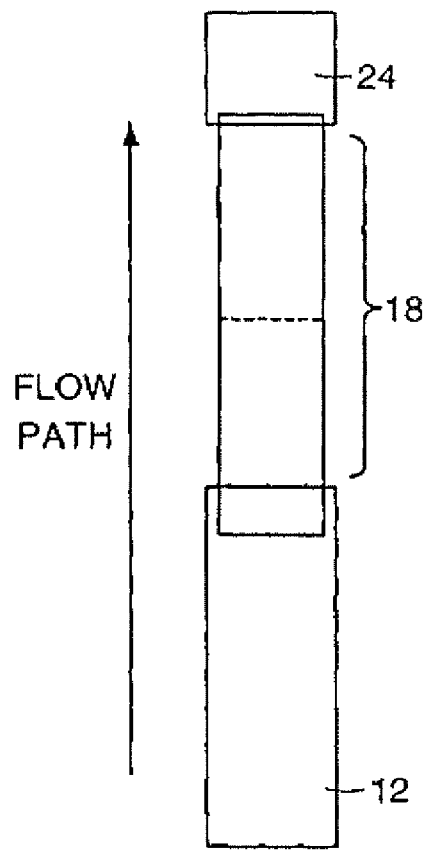
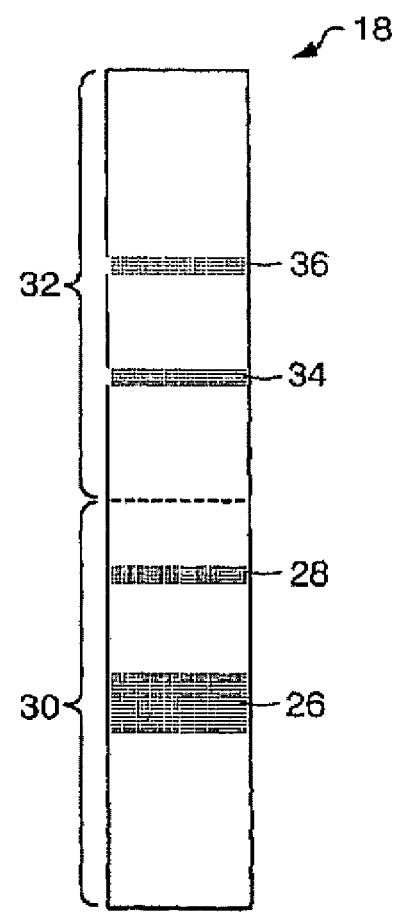
FIG. 3         FIG. 4
FIG. 5

DIAGNOSTIC DETECTION DEVICE

CROSS-REFERENCE TO RELATED APPLICATIONS

The present application is a division of U.S. patent application Ser. No. 11/681,061, filed Mar. 1, 2007, the disclosure of which is incorporated herein by reference in its entirety.

FIELD OF THE INVENTION

The invention relates to diagnostic assays for analytes in a liquid sample. In particular, the invention relates to a device for detecting an analyte in a bodily fluid using a lateral flow test cell that exhibits improved detection.

BACKGROUND

Many types of ligand-receptor assays have been used to detect the presence of various substances in body fluids, such as urine, saliva, or blood. Many tests are designed to make a quantitative determination, but in many circumstances all that is required is a qualitative positive/negative indication. Examples of such qualitative assays include blood typing, pregnancy testing, and many types of urinalysis. For these tests, visually observable indicia, such as the presence of agglutination or a color change, are preferred.

The positive/negative assays must be very sensitive because of the often small concentration of the ligand of interest in the test fluid. False positives can be troublesome, particularly with agglutination and other rapid detection methods such as dipstick and color change tests. Because of these problems, sandwich assays and other sensitive detection methods which use metal sols or other types of colored particles have been developed.

U.S. Pat. No. 6,485,982, which is incorporated herein by reference in its entirety, describes a diagnostic test cell formed of an elongate outer casing which houses an interior permeable material (such as glass fiber) capable of transporting an aqueous solution by capillary action, wicking, or simple wetting. The casing defines a sample inlet, and interior regions, which are designated as a test volume and a reservoir volume. The reservoir volume is disposed in a section of the test cell spaced apart from the inlet and is filled with sorbent material. The reservoir acts to receive liquid transported along a flow path defined by the permeable material and extending from the inlet and through the test volume. In the test volume is a test site comprising a first protein having a binding site specific to a first epitope of the ligand immobilized in fluid communication with the flow path (e.g., bound to the permeable material or to latex particles entrapped in or bonded to the permeable material). A window, such as a hole or transparent section of the casing, permits observations of the test site through the casing wall. The method of use of the test cell requires the use of a conjugate comprising a second protein bound to colored particles, such as a metal sol or colloid, preferably gold. The conjugate can take two distinct forms, depending on whether the assay is designed to exploit the "sandwich" or "competitive" technique.

U.S. Pat. No. 7,045,342, which is incorporated herein by reference in its entirety, describes a diagnostic device including a biphasic chromatographic medium. The biphasic substrate is formed of a release medium joined to a capture medium located downstream of the release medium. The release and capture media preferably comprise two different materials, or phases, having different specific characteristics. The two phases are joined together to form a single liquid path such that a solvent front can travel unimpeded from the proximal (upstream) end of the release medium to the distal (downstream) end of the capture medium.

Although diagnostic devices, such as those described above, show improvements over the art, there still remains a need for test devices providing greater accuracy and detection of even lower analyte levels in the sample fluid. For example, in the field of pregnancy testing, accurate and rapid detection of low levels of hCG is desired to allow consumers to confirm pregnancy early after conception has occurred.

SUMMARY OF THE INVENTION

The present invention provides greater accuracy and better low analyte level detection than previously possible in the art. In particular, the invention provides a diagnostic detection device that is capable of detecting the presence of analytes in bodily fluids, even when the analytes are present in very low levels.

In certain embodiments, the invention comprises a diagnostic device including a label component that provides for analyte detection at even low analyte concentrations. The invention generally comprises a device for detecting an analyte in a liquid sample deposited on a first portion of the device for transport to a second portion of the device that is in fluid contact with the first portion. In specific embodiments the device comprises, in the first portion thereof, a labeled conjugate comprising a binding member reactive with a first epitope of the analyte and a label comprising a gold colloid. Preferably, the gold colloid has a mean particle size of about 60 nm to about 80 nm prior to formation of the labeled conjugate. The device further comprises, in the second portion thereof, a capture component that is directly or indirectly reactive with a second epitope of the analyte.

In other embodiments, the invention comprises a diagnostic device including a capture component that provides for analyte detection at even low analyte concentrations. The invention preferably comprises a device for detecting an analyte in a liquid sample, wherein the device comprises a biphasic substrate. In specific embodiments, the biphasic substrate comprises a release medium formed of a first material and a capture medium in fluid communication with the release medium and formed of a second, different material.

In a preferred embodiment, the release medium comprises a labeled conjugate comprising a label and a binding member reactive with a first epitope of the analyte. The release medium further comprises a capturable conjugate comprising a binding member having a site reactive with a second epitope of the analyte and a capturable component, such as biotin. Accordingly, in diagnostic tests wherein a liquid sample for testing includes the analyte to be detected, the analyte produces a complex comprising the labeled conjugate, the analyte for detection, and the capturable conjugate.

The capture medium preferentially comprises a capture site that includes a capture component for capturing the complex described above. In a specific embodiment, the capture site has immobilized thereon a capture component comprising polymerized streptavidin.

The invention is particularly characterized in that multiple aspects of the invention can be combined to provide a diagnostic device including multiple elements useful for providing improved test results, particularly improved accuracy, improved ability to detect low levels of test analyte, and overall improved test results. Preferentially, the invention combines an enhanced label component with an enhanced capture component to improve the overall efficiency of the inventive diagnostic device, particularly in relation to the sensitivity of the diagnostic device.

In one embodiment, the invention comprises a device for detecting an analyte, wherein the device comprises a biphasic substrate, which comprises a release medium formed of a first material and a capture medium in fluid communication with the release medium and formed of a second, different material. The release medium preferably comprises both a labeled conjugate and a capturable conjugate. The labeled conjugate comprises a binding member reactive with a first epitope of the analyte and a label comprising a gold colloid having a mean particle size of about 50 nm to about 100 nm prior to formation of the labeled conjugate. The capturable conjugate comprises a binding member having a site reactive with a second epitope of the analyte, such that if the analyte is present in the sample, the analyte produces a complex comprising the gold colloid labeled conjugate, the analyte for detection, and the capturable conjugate. The capture medium preferably comprises a capture site for capturing the complex, the capture site having immobilized thereon a capture component comprising polymerized streptavidin.

In another aspect, the present invention provides various methods for determining the presence of an analyte in a liquid sample. In one embodiment, the method comprises providing a device for detecting an analyte in a liquid sample deposited on a first portion of the device for transport to a second portion of the device. Preferably the device comprises a biphasic substrate comprising a release medium and a capture medium. The release medium is generally formed of a first material and comprises a labeled conjugate comprising a binding member reactive with a first epitope of the analyte and a label comprising colloidal gold particles having a mean particle size of at least about 50 nm prior to formation of the labeled conjugate. The release medium further comprises a capturable conjugate comprising a binding member having a site reactive with a second epitope of the analyte, such that if the analyte is present in the sample, a complex is formed comprising the gold colloid labeled conjugate, the analyte for detection, and the capturable conjugate. The capture medium is in fluid communication with the release medium and is typically formed of a second, different material, the capture medium comprising a capture site for capturing the complex, the capture site having immobilized thereon a capture component comprising polymerized streptavidin. In preferred embodiments, the method further comprises adding a liquid sample to the first portion of the device and allowing the liquid sample to flow across the release medium and the capture medium. According to the method, the presence of the analyte in the liquid sample is determined by visual inspection of the capture medium, wherein the presence of the analyte is indicated by the presence of color development at the capture site caused by the binding of the streptavidin capture component with the complex formed of the gold colloid labeled conjugate, the analyte for detection, and the capturable conjugate.

In another embodiment, the method of the invention comprises providing an analyte detection device comprising a substrate with a first portion comprising colloidal gold having a mean particle size of 50 nm to 100 nm releasably immobilized thereon and a second portion in fluid communication with the first portion and comprising a capture component immobilized thereon. The method further comprises adding a liquid sample to the first portion of the device, allowing the liquid sample to flow across the first portion and the second portion of the substrate, and determining the presence of the analyte in the liquid sample by visual inspection of the second portion of the substrate. Preferably, the presence of the analyte is indicated by the presence of color development in the area wherein the capture component is immobilized caused by accumulation of the colloidal gold.

In further embodiments, the method of the invention is specifically directed to the detection of human chorionic gonadotropin (hCG). A preferred embodiment comprises the following steps: providing an hCG detection device comprising a substrate with a first portion comprising colloidal gold having a mean particle size of 50 nm to 100 nm, more preferably 55 nm to 85 nm and still more preferably 60 nm to 75 or 80 nm, releasably deposited thereon and a second portion in fluid communication with the first portion and comprising polymerized streptavidin immobilized thereon; adding a liquid sample to the first portion of the device; allowing the liquid sample to flow across the first portion and the second portion of the substrate; and determining the presence of the hCG in the liquid sample by visual inspection of the second portion of the substrate, wherein the presence of the hCG is indicated by the presence of color development in the area wherein the polymerized streptavidin is immobilized caused by accumulation of the colloidal gold.

In still another embodiment, the method of the invention is specifically directed to predicting ovulation in a subject via detection of changes in levels of leuteinizing hormone (LH). One preferred embodiment comprises the following steps: providing an LH level detection device comprising a substrate with a first portion comprising colloidal gold having a mean particle size of 50 nm to 100 nm releasably deposited thereon and a second portion in fluid communication with the first portion and comprising polymerized streptavidin immobilized thereon; adding a liquid sample to the first portion of the device; allowing the liquid sample to flow across the first portion and the second portion of the substrate; and determining the presence of an LH change evidenced by an LH level above a predetermined LH threshold in the liquid sample by visual inspection of the second portion of the substrate, wherein the presence of the LH level above the predetermined threshold is indicated by the presence of color development in the area wherein the polymerized streptavidin is immobilized caused by accumulation of the colloidal gold.

In yet another embodiment, the method of the invention is specifically directed to determining the female fertility status of a subject via detection of follicle stimulating hormone (FSH). One preferred embodiment comprises the following steps: providing an FSH detection device comprising a substrate with a first portion comprising colloidal gold having a mean particle size of 50 nm to 100 nm releasably deposited thereon and a second portion in fluid communication with the first portion and comprising polymerized streptavidin immobilized thereon; adding a liquid sample to the first portion of the device; allowing the liquid sample to flow across the first portion and the second portion of the substrate; and determining the presence of FSH below a predetermined FSH threshold in the liquid sample by visual inspection of the second portion of the substrate, wherein the presence of the FSH below the predetermined threshold is indicated by the presence of color development in the area wherein the polymerized streptavidin is immobilized caused by accumulation of the colloidal gold.

Still another embodiment of the inventive method makes particular use of the polymerized streptavidin described herein. In particular, the invention provides a method for determining the presence of an analyte in a liquid sample comprising providing a device for detecting an analyte in a liquid sample. The device preferably comprises a release medium comprising a labeled conjugate formed of a binding member reactive with a first epitope of the analyte and a label, and further comprises a capturable conjugate comprising a binding member having a site reactive with a second epitope of the analyte such that if the analyte is present in the sample, the analyte produces a complex comprising the labeled conjugate, the analyte, and the capturable conjugate. The device further comprises a capture medium in fluid communication with the release medium that comprises polymerized streptavidin immobilized thereon. The method further comprises adding a liquid sample to the device, allowing the liquid sample to flow across the release medium and the capture medium, and determining the presence of the analyte in the liquid sample by visual inspection of the capture medium. Preferably, the presence of the analyte is indicated by the presence of color development caused by the binding of the polymerized streptavidin component with the complex formed of the labeled conjugate, the analyte, and the capturable conjugate.

BRIEF DESCRIPTION OF THE DRAWINGS

The present invention is particularly described in reference to the following figures; however, such figures are provided to illustrate only preferred embodiments of the invention, and the invention is not intended to be limited thereto.

FIG. 3 is a schematic top view of a test device according to one embodiment of the invention illustrating a sample absorbent, a biphasic substrate, and a reservoir material;

FIG. 4 is a schematic top view of a biphasic substrate according to one embodiment of the invention;

FIG. 5 is a schematic side view of the embodiment of a test device according to the invention illustrated in FIG. 2;

DETAILED DESCRIPTION OF THE INVENTION

Figure 1A:
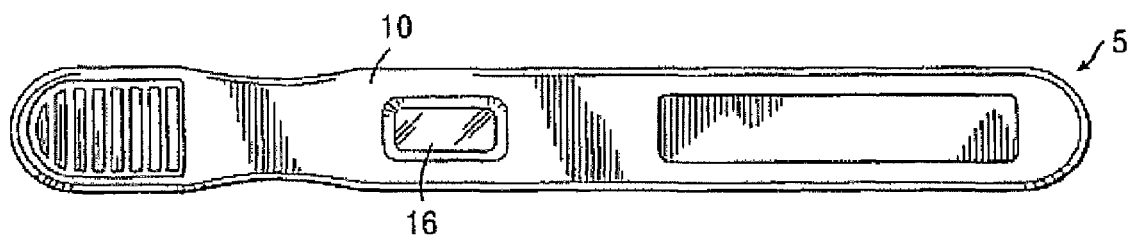
FIG. 1A is a top view of an embodiment of a diagnostic test device according to the present invention.
Figure 1B:
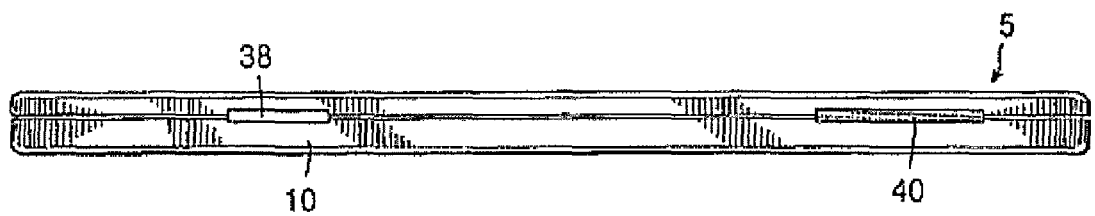
FIG. 1B is a longitudinal side view of an embodiment of a diagnostic test device according to the present invention.
Figure 1C:
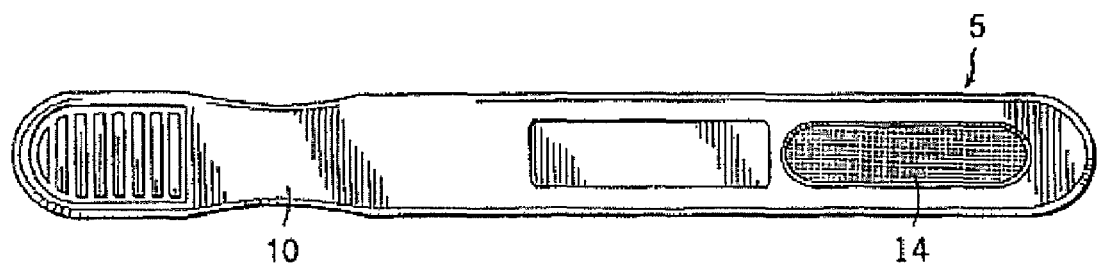
FIG. 1C is a bottom view of an embodiment of a diagnostic test device according to the present invention.
Figure 1D:
FIG. 1D is a tail end view of an embodiment of a diagnostic test device according to the present invention.
Figure 1E:
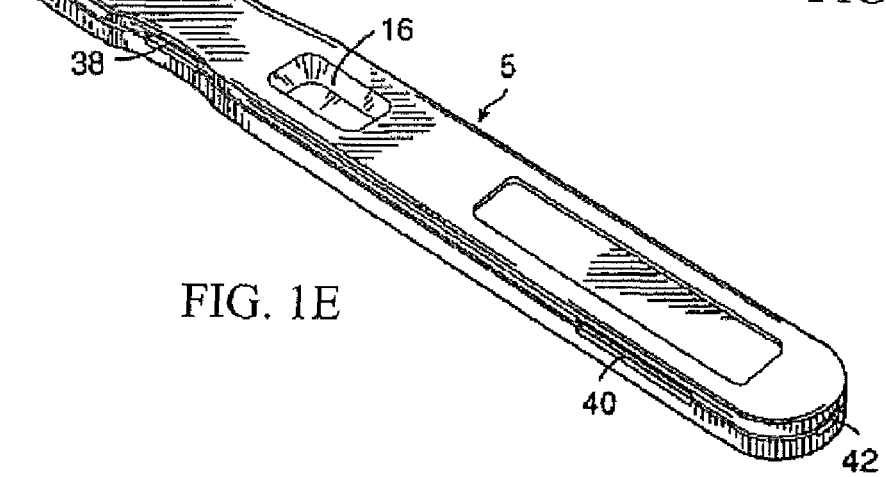
FIG. 1E is a top perspective view an embodiment of a diagnostic test device according to the present invention.
Figure 2A:
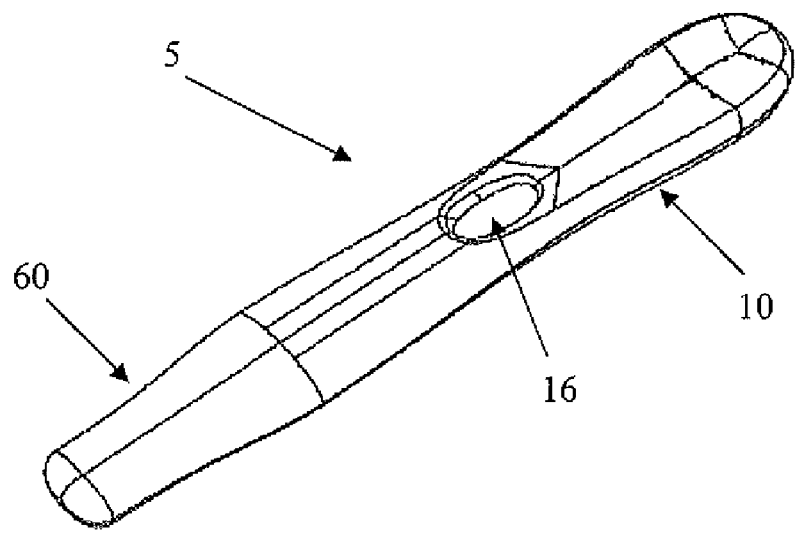
FIG. 2A is a front, top, left side perspective view of a preferred embodiment of a diagnostic test device according to the present invention.
Figure 2B:
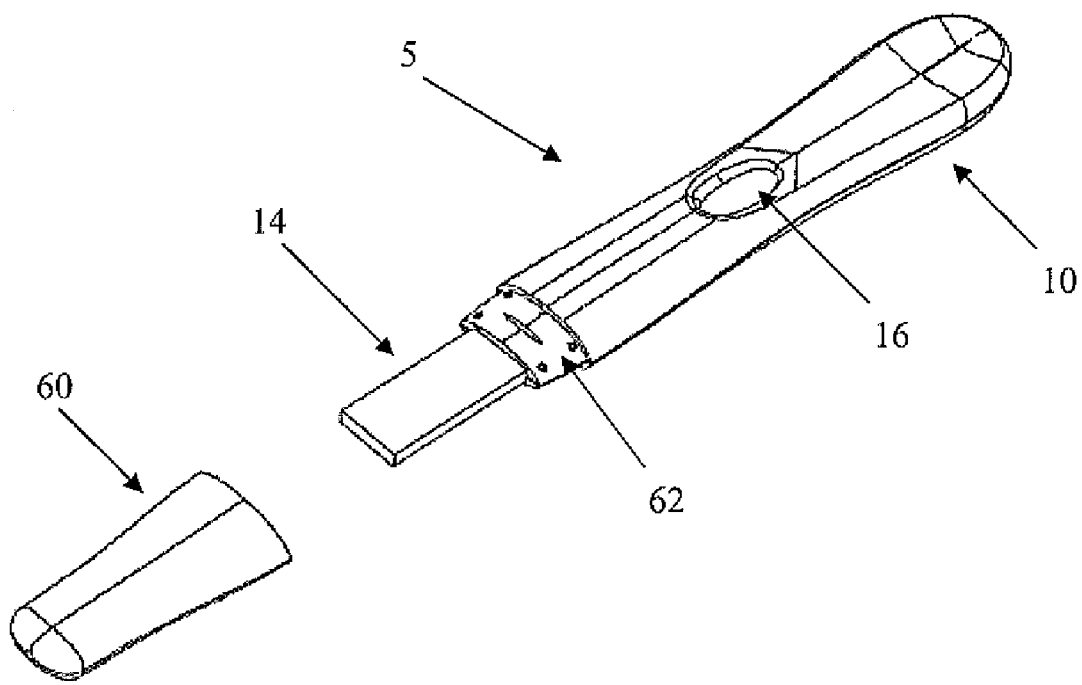
FIG. 2B illustrates the test device embodiment from FIG. 2A with the cap thereof removed.
Figure 2C:
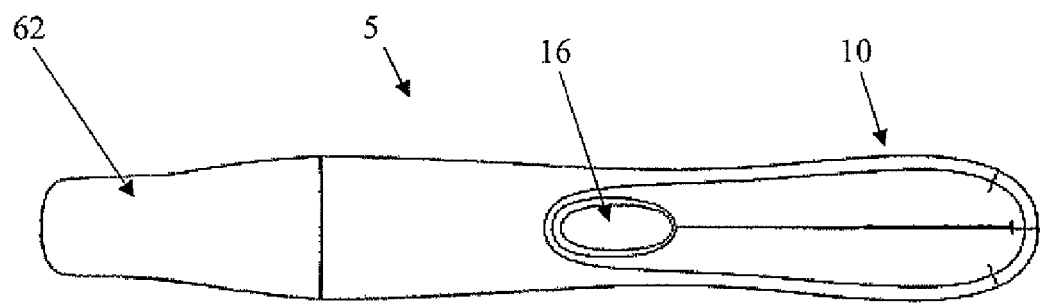
FIG. 2C is a top plan view of the test device embodiment from FIG. 2A.
Figure 2D:
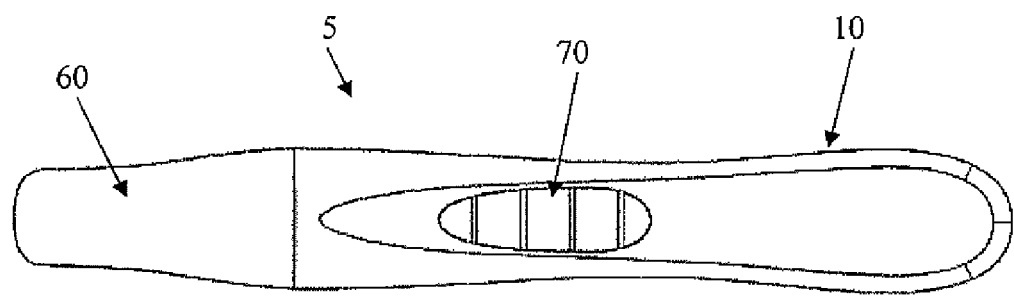
FIG. 2D is a bottom plan view of the test device embodiment from FIG. 2A.
Figure 2E:
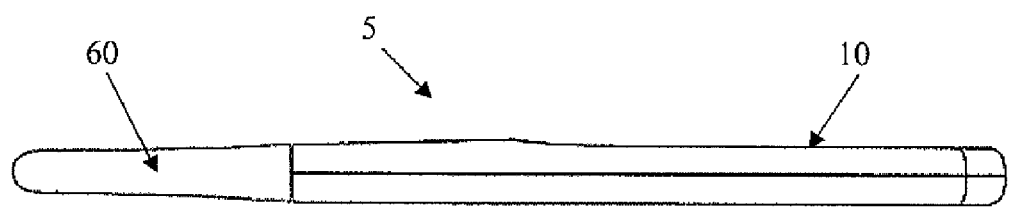
FIG. 2E is a left side elevational view of the test device embodiment from FIG. 2A.

The present inventions now will be described more fully hereinafter with reference to specific embodiments of the invention and particularly to the various drawings provided herewith. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The invention generally comprises a test cell for conducting an immunoassay and a process using the test cell and a conjugate comprising a labeled component. The inventive detection device is characterized in that it increases the efficiency and effectiveness of a simplified test that untrained personnel can use to reliably assay a liquid sample for the presence of extremely small quantities of a particular ligand while avoiding false positives. The invention is ideal for use in over-the-counter assay test kits which will enable a consumer to self diagnose, for example, pregnancy, ovulation, venereal disease, and other disease, infection, or clinical abnormality which results in the presence of an antigenic marker substance in a body fluid, including determination of the presence of drugs and their metabolites or toxins. The assay process and the test device are engineered specifically to detect the presence of a pre-selected individual ligand present in bodily fluids or other fluids.

The inventive diagnostic device can be used to detect any analyte which has heretofore been assayed using known immunoassay procedures, or known to be detectable by such procedures, using polyclonal or monoclonal antibodies or other proteins comprising binding sites for ligands. Various specific assay protocols, reagents, and proteins can be used according to the present the invention such as, for example, those described in U.S. Pat. No. 4,313,734, which is incorporated herein by reference.

The diagnostic device is generally described herein in terms of evaluating a sample for the presence of an analyte therein. In relation to specific embodiments, the analyte may be specifically described as being a ligand. Such description in relation to a specific embodiment should not be viewed as limiting the invention. Rather, the analyte for detection in a sample can comprise a variety of detectable materials, and the term ligand only refers to certain embodiments of detectable materials within a liquid sample.

The diagnostic device of the invention preferably makes use of a conjugate comprising a protein bound to a label component (which can specifically be colored particles, such as a metal sol or colloid, preferably gold). The conjugate can take two distinct forms, depending on whether the assay is designed to exploit the "sandwich" or "competitive" technique.

In embodiments wherein the diagnostic detection device of the invention makes use of a sandwich technique, the protein used in the detection comprises a site which binds to an epitope on the ligand for detection. The protein preferably has a label component bound thereto to form a conjugate, which reacts with the ligand to form a complex in the liquid sample. The ligand bound with the conjugate reacts with a binding protein to form a "sandwich" of the binding protein, ligand, conjugated protein, and label component. This sandwich complex is progressively produced as the test liquid with the ligand therein continuously moves along the test strip in the diagnostic device. As more and more conjugate is immobilized, the label components aggregate and become visible through the viewing window, indicating the presence of ligand in the liquid sample.

In embodiments using the competitive technique, the binding protein reacts with the conjugating protein in competition with the ligand. The binding protein comprises, for example, an authentic sample of the ligand or a fraction thereof which has comparable affinity for the conjugated protein. Generally, a test site is present in the device, and as the liquid sample is transported in contact with the test site, ligand, if any, and the conjugate compete for sites of attachment to the conjugating protein. If no ligand is present, label particles aggregate at the test site, and the presence of color indicate the absence of detectable levels of ligand in the sample. If ligand is present, the amount of conjugate which binds at the test site is reduced, and no color, or a paler color, develops.

The conjugate used in the diagnostic device can be formed in various ways. For example, the test liquid can be mixed with the conjugate outside the test cell (i.e., prior to placement of the test liquid into the test cell). In another embodiment, the conjugate can be disposed on the test strip permeable material (such as in freeze-dried or other preserved form) between the inlet and the test site, and the sample liquid reconstitutes the conjugate as it passes along the flow path.

The inventive diagnostic device can include one or more standards or internal controls that allow for determination of whether signal development (e.g., color development) is a true indication of the presence or absence of ligand in the sample or is simply an artifact, such as caused by nonspecific sorption. For example, in one embodiment employing the sandwich technique, the standard consists of a negative control site, preferably disposed adjacent the test site, and visible through a second window proximate the first. The negative control site preferably is prepared identically to the test site, except immobilization of the binding protein is omitted. Therefore, although the conjugate will reach the control site, it aggregates due only to non-specific binding. If the test site is not appreciably more intense in color than the control site, the assay is considered negative.

In another embodiment, the diagnostic device may include a positive control. Thus, when exploiting the sandwich technique, the cell may have an authentic sample of the ligand for detection immobilized at a control site. If no color develops at this control site, the assay is considered inconclusive. When exploiting the competitive technique, the development of color at the positive control site means the assay results are inconclusive.

In yet another embodiment, which is particularly useful when the diagnostic device comprises a biphasic test strip medium, the biphasic medium comprises a control site disposed on the capture medium downstream of the capture site. The control site has immobilized thereon an agent capable of capturing the labeling antibody. The primary function of the control site is to capture and immobilize antibody which has not been captured at the capture site. In a preferred embodiment, the control site has immobilized thereon polyclonal antisera specific for the labeling antibody. Indication of the presence of the label component at the control site indicates proper functioning of the test, irrespective of the presence or absence of analyte in the sample. Both the capture and control sites must be visible through the window of the casing.

In one embodiment of the invention, the diagnostic device is particularly useful for detecting the presence of a pregnancy-indicating ligand, such as human chorionic gonadotropin (hCG), follicle stimulating hormone (FSH), or leuteinizing hormone (LH), in a test sample, such as a human urine sample. Generally, the test sample and the protein-label conjugate move along a flow path leading to contact with a test site comprising the immobilized binding protein that is specific to an epitope of the ligand, and preferably also to contact with a control site, as described above. Placement of the test cell in the sample, or application of the sample to the inlet, initiates flow, and the result is read by observing color development at the test site, or by comparing the color of the test site and control site.

In a preferred embodiment, the inventive diagnostic device incorporates a biphasic chromatographic medium (or test strip) which enhances the speed and sensitivity of the assay. Generally, a biphasic substrate element useful according to the invention comprises a release medium joined to a capture medium located downstream of the release medium. The release and capture media preferably comprise two different materials or phases having different specific characteristics. The two phases are joined together to form a single liquid path such that a solvent front can travel unimpeded from the proximal (upstream) end of the release medium (which can be defined as a first portion of the diagnostic device) to the distal (downstream) end of the capture medium (which can be defined as a second portion of the diagnostic device).

Reagents for detecting, labeling, and capturing the analyte of interest are disposed on the release and capture media. Located on the release medium is a labeled conjugate comprising a binding member reactive with a particular site (sometimes referred to as a "first epitope") on the analyte of interest. The labeled conjugate further comprises a detectable marker (or label), preferably colloidal gold. A capturable conjugate is located on the release medium downstream of the labeled conjugate, which conjugate comprises a binding member reactive with another particular site (sometimes referred to as a "second epitope") on the analyte of interest. The first epitope and the second epitope are preferably different sites on the analyte. The capturable conjugate also comprises one member of an affinity pair and is capable of forming a complex with the labeled binding member and the analyte. The labeled conjugate and the capturable conjugate both are releasably bound to the release medium such that when the solvent front created by the liquid sample being analyzed passes through the release medium, the labeled conjugate and the capturable conjugate both become reconstituted by the liquid and flow with the solvent along the liquid path. In operation, if any analyte is present in the liquid sample, it reacts first with the labeled conjugate, then with the capturable conjugate as the front advances along the liquid path to form a diffusible sandwich which is then transported by capillary action. Thus, by the time the solvent front reaches the capture medium section of the biphasic material, the capturable sandwich complex has formed.

The capture medium contains the reagents used to capture the sandwich complex described above. Generally, the reagents are located on a capture site and comprise the other member of the affinity pair specific for the capturable conjugate and a reagent specific for the labeled binding member. Upon diffusion into the capture medium, the diffusible sandwich becomes concentrated by the interaction of the capture affinity member with the capturable affinity moiety yielding a visual signal. The affinity member is immobilized, preferably by simple adsorption, at the capture site, and does not advance with the solvent front.

The release medium is formed from a substance which allows for release of indicator reagents. In certain embodiments, the release medium comprises a bibulous, hydrophilic material, such as absorbent materials. Preferred materials for use as a release medium include, but are not limited to, cotton linter, cellulosic materials, or materials made of cellulose together with a polymeric fibrous material, such as polyamide or rayon fibers, and glass fiber material. The primary function of the release medium is first to support and to subsequently release and transport various immunological components of the assay, such as a labeled conjugate and a capturable conjugate, both of which have specific affinity for the analyte of interest. This release and transport occurs during routine operation of the assay. Generally, the release medium can be formed of any material capable of performing the function of holding, releasing, and transporting various immunological parts of the test such as the labeled test component.

Specific, non-limiting examples of materials useful in forming the release medium include: cotton linter paper, such as S&S 903 and S&S GB002 (available from Schleicher and Schuell, Inc., Keene, N.H.), and BFC 180 (available from Whatman, Fairfield, N.J.); cellulosic materials, such as Grade 939 made of cellulose with polyamide, Grade 989 made of cellulose blend fiber, and Grade 1278 and Grade 1281 made of cellulose and rayon with polyamide (available from Ahlstrom Corporation, Mt. Holly Springs, Pa.); and glass fiber, such as Lydall borosilicate (available from Lydall, Inc., Rochester, N.H.). The release medium preferably is coated with an aqueous solution containing bovine serum albumin (BSA) and a nonionic surfactant, such as Triton X-100 (available from Rohm & Haas Co., Philadelphia, Pa.) in order to prevent nonspecific binding and facilitate release of the diffusible reagents. A combination of about 3% BSA and about 0.1% Triton X-100 is useful for this purpose.

The capture medium is formed from a substance which permits immobilization of reagents for detection of the presence of analyte in the test fluid. The capture medium generally comprises hydrophilic polymeric materials, such as microporous films or membranes, which permit protein reagents to be immobilized directly on the membrane by passive adsorption without the need for chemical or physical fixation. Of course, the use of chemical or physical fixation is not precluded by the invention, and any known method for immobilizing the reagents to the membrane can be used.

Non-limiting examples of materials useful as the capture medium comprise a microporous polymeric film of nitrocellulose, nylon (e.g., nylon 66), or similar materials, or combinations of such materials. Materials for use as the capture medium preferably have a pore size in the range of from about 5 µm to about 20 µm. In specific embodiments, the nitrocellulose membrane may be nitrocellulose alone or a mixed ester of nitrocellulose, such as in combination with an ester of nitric acid and/or other acids. The nitrocellulose membrane preferably is coated or laminated onto a translucent or transparent polymeric film to provide physical support for the membrane.

In a preferred embodiment, a nitrocellulose polymer which has been cast onto a polyester film, such as MYLAR™, is used. Alternatively, a nitrocellulose membrane laminated onto a polyester film also may be used, although other backing materials besides polyester may be used. Pre-laminated or pre-cast sheets useful in the present invention are commercially available, for example, from Millipore Corporation, Bedford, Mass. and Sartorius Corporation, Edgewood, N.Y. Both media are in the form of planar strips, which are joined together to form a single flow path.

In one embodiment, the release medium and capture medium are joined by overlapping the downstream edge of the release medium over the upstream edge of the capture medium, then adhering the resulting biphasic material to a clear polymer film or sheet, thereby holding the media in place. The overlapping region allows for the efficient and rapid transfer of analyte containing fluid from the release medium to the capture medium.

While the rapid transfer associated with the overlapping region is useful, the manufacturing issues associated with reproducibly generating a small overlapping region, such as necessary with small diagnostic devices, can be difficult. Therefore, in certain embodiments, the invention also provides a test device having a biphasic design as described herein but wherein the release medium and the capture medium do not overlap but rather are connected by a non-overlapping butt joint. In such embodiments, the fluid front moving along the test strip is transferred from the release medium to the capture medium through bridging the non-overlapping region by capillary action.

Beneficially, and optionally, the butt joining of the phases maintains the same efficacy of the overlapping of the phases, even after accelerated aging of the devices. Thus, the use of a butt joint simplifies the manufacture of the present test device without any loss of performance in the device.

Methods for manufacturing a biphasic chromatographic medium are described in U.S. Pat. No. 5,846,835, which is incorporated herein by reference. Briefly, the release medium and capture medium are positioned to be adjoining one another, and an adhesive is disposed on the back of each (the back being the side opposite that which will receive the reagents). The adhesive may be any pressure sensitive or hot melt adhesive which does not fill the pores of the release or capture medium, thereby permitting unimpeded flow of the solvent front through the media. Adhesives useful in the present invention are commercially available, for example, from Adhesives Research Corp. In one embodiment, the adhesive is disposed on a clear polymer backing. The release and capture media then are passed through the laminating rollers of a laminating machine together with the backed adhesive, forming a laminate of the capture and release media, the adhesive and the polymer backing. The resulting laminated biphasic substrate then is ready to receive the reagents, which are deposited as continuous "stripes" onto the top of the substrate. Once the reagents have been deposited and dried, if necessary, the substrate is cut into the desired size. One embodiment of a biphasic test strip for used according to the present invention is illustrated in FIG. 3, and is further described below.

The diffusible and non-diffusible reagents can be applied to the release and capture media, respectively, by any suitable technique. In one embodiment, the diffusible antibody reagents are applied to the release medium by direct application onto the surface of the medium and dried to form a narrow band. The non-diffusible reagents preferably are applied to the capture medium by passive adsorption.

The chromatographic substrate specifically can be disposed within a test device, which comprises, at a minimum, a housing encasing the chromatographic substrate for conducting the assay. One useful housing configuration is shown in U.S. Pat. No. D361,842, which is incorporated herein by reference. Another embodiment of the casing is described in U.S. Pat. No. 5,739,041, which is incorporated herein by reference.

In a preferred embodiment, the diagnostic device comprises a casing defining a sample inlet, a test volume, and reservoir volume. Disposed within the casing are a sample absorbent, the biphasic chromatographic substrate, and reservoir absorbent. The sample absorbent is preferentially disposed within the casing and extending to the exterior thereof. Located downstream of the sample absorbent is the biphasic chromatographic substrate comprising a release medium and a capture medium joined together to form a single liquid path. The release and capture media can be laminated onto a transparent plastic film or sheet.

The sample absorbent preferably is a bibulous hydrophilic material which facilitates absorption and transport of a fluid sample to the biphasic chromatographic medium. Such materials may include cellulose acetate, hydrophilic polyester, and other materials having similar properties. Further, a combination of absorbent materials also may be used. Non-limiting examples of useful materials include bonded cellulose acetate, bonded polyolefin, or hydrophilic polyester, such as those materials commercially available from Filtrona Fibertec Company (Colonial Heights, Va.). Other useful materials include absorbent matrices, such as Grade 939, Grade 989, Grade 1278, or Grade 1281, available from Ahlstrom Corporation. The sample absorbent preferably is coated with a buffered solution containing BSA and a nonionic surfactant, such as Triton X-100. The presence of BSA and surfactant minimize non-specific absorption of the analyte. A concentration of about 1% BSA and about 0.2% surfactant in tris buffer is effective for this purpose.

By providing a reservoir of sorbent material disposed beyond the chromatographic substrate, a relatively large volume of the test liquid and any analyte it contains can be drawn through the test area to aid sensitivity. The reservoir material preferably comprises a hydrophilic material which may be the same as the upstream sample absorbent. The reservoir absorbent generally facilitates capillary action along the chromatographic substrate and absorbs excess liquid contained within the device. The reservoir absorbent preferably compromises absorbent paper made from cotton long linter fibers, such as S&S 300, S&S 470 and S&S 900, (available from Schleicher & Schuell, Inc.) or cellulosic materials, such as Grade 3MM (available from Whatman) and Grade 320 (available from Ahlstrom).

Broadly, the device and method of the invention can be used to detect any analyte which has heretofore been assayed using known immunoassay procedures, or is detectable by such procedures, using polyclonal or monoclonal antibodies or other proteins. Various specific assay protocols, reagents, and analytes useful in the practice of the invention are disclosed in U.S. Pat. No. 4,313,734, and U.S. Pat. No. 4,366,241, both of which are incorporated herein by reference.

In using the diagnostic device according to this embodiment of the invention, the proximal end of the biphasic substrate is contacted with the liquid sample being analyzed. The casing of the device may be configured to permit direct contact with a body fluid or as a dipstick for dipping in a container of body fluid or other test solution. The liquid sample travels impelled by surface effects such as by capillary action along the liquid path formed by the substrate. More specifically, the test sample passes through the biphasic chromatographic substrate and into reactive contact with the test site (and optionally one or more control sites). Preferably, at least the test site is visible to a user, such as through one or more windows in the device's exterior casing. In a preferred embodiment, the labeled binding member specific for the analyte is disposed in preserved form on the release medium in the flow path within the device.

If the analyte of interest is present in the sample, it passes through the inlet and the interior of the device where it sequentially reacts with the labeled conjugate and the capturable conjugate with the affinity agent, thereby forming the capturable complex. The complex formed by the analyte, labeled conjugate, and the capturable conjugate then reacts with the immobilized capture component at the capture site, the capture component being specific for the affinity agent on the capturable conjugate. This process results in the labeled complex accumulating at the capture site. The presence of the analyte is determined by observing the presence of the detectable marker at the capture site. If no analyte is present in the sample, the capturable complex does not form and no detectable marker will be present at the capture site. If a control site is present, the unbound complex or the free labeled binding member will accumulate at the control site.

Illustrations of one embodiment of a test device 5 according to the present invention are shown in FIGS. 1A-E. The test device 5 comprises an outer, molded casing 10 which defines a hollow, elongate enclosure. The casing 10 includes a test liquid inlet 14 and an opening 16 comprising a window through which the capture site (and control site, if applicable) is visible. As illustrated in FIGS. 1A-E, the window 16 is disposed on a side of 30 the casing 10 opposite the sample inlet 14. This configuration reduces the incidence of contamination of the test site which is disposed in the interior of casing 10 and is exposed through the window 16. The casing 10 further defines vent openings 38, 40, and 42 located along the sides and at the distal end of the casing 10. The vent opening 38 reduces the incidence of "vapor lock" within the device during use. The presence of the openings 40 and 42 help to reduce "flooding" of the chromatographic substrate, which may occur when the user applies too much sample to the device.

A preferred embodiment of the test device 5 is illustrated in FIGS. 2A-E. As seen therein, the test device 5 comprises an outer, molded casing 10 which defines a hollow, elongate enclosure. The casing 10 includes an opening 16 comprising a window through which the capture site (and control site, if applicable) is visible. The test device 5 further includes a test liquid inlet 14, which is covered by a removable cap 60. In this embodiment, the test liquid inlet 14 is external to the casing 10 and is covered by the cap 60 except when in use. Providing the test liquid inlet 14 external to the casing 10 allows for ease of application of the test liquid to the test device 5, such as by placing the test liquid inlet 14 in the path of a urine stream or dipping in a container holding the test liquid. The cap 60 is re-attachable (such as "snap-fitting" onto the lip 62 extending from the casing 10) and can be replaced after application of the test liquid to avoid contamination of the sample while the test is proceeding. The test liquid inlet 14 external to the casing can be a portion of the absorbent material 12, as described below. In further embodiments, the test liquid inlet 14 can be a portion of the biphasic chromatographic substrate 18. The casing 10 further includes a test strip support 70 located on the bottom surface of the casing 10.

A specific embodiment of the assay materials for use according to the invention is illustrated in FIG. 3. When the device is fully assembled, the assay materials of FIG. 3 preferably are disposed inside a casing. The assay materials comprise an absorbent material 12, a biphasic chromatographic substrate 18, and a reservoir material 24. The assay materials and the interior of the casing together define a flow path. When the inlet 14 is disposed within or otherwise in contact with a liquid sample, the liquid is transported by capillary action, wicking, or simple wetting along the flow path downstream through the absorbent 12, along the chromatographic substrate 18, and into the reservoir 24, generally as depicted by the arrow. The absorbent material also serves as a filter which can remove from impure test samples particulate matter and interfering factors.

Illustrated in FIG. 4 is a biphasic chromatographic substrate 18, comprising a release medium 30 and a capture medium 32. The horizontal dashed line represents the interface between the release medium 30 and the capture medium 32. As previously noted, this interface can be in the form of an overlapping relationship. Alternatively, the release medium 30 can be butted up to the capture medium 32. Releasably disposed on the release medium 30 is a band 26 of labeled binding member, e.g., an antibody-metal sol. In one embodiment, the labeled biding member is in dehydrated form. As the liquid sample moves past the band 26, the labeled binding member becomes entrained in the liquid, reconstituted (in the case of a dehydrated binding member), and reacts or competes with any analyte present in the liquid sample. Disposed downstream of the labeled binding member is a band 28 of preferably dehydrated capturable complex. The capturable complex comprises a binding member which binds to a second epitope of the analyte, e.g. an antibody, and a capturable affinity component, e.g. biotin. The capturable complex also becomes entrained in the liquid sample as it advances along the substrate 18.

Immobilized on the capture medium 32 are, respectively, the capture site 34 and the control site 36. In FIG. 4, the control and capture sites are illustrated as being disposed serially along the flow path. Alternatively, the control and capture site or sites may be disposed side by side or in other spatial relationships. The capture site 34 comprises a preselected quantity of a capture affinity member specific for the capturable affinity component disposed on the release medium. For example, when the capturable affinity member is biotin, the capture component may be streptavidin. Of course, any such complementary system of components could be used in place of biotin and streptavidin. The control site 36 typically comprises immobilized antisera or antibody specific for the labeled binding member and is thus also capable of binding the labeled binding member.

A side view of one embodiment of the operative portion of the assay materials is schematically illustrated in FIG. 5. As shown, the absorbent material 12 is disposed proximate the release medium 30, and overlaps the release medium 30 at one end. The release medium 30 in turn overlaps the capture medium 32, which is disposed distal to the release medium 30. Again, the release medium 30 and the capture medium 32 may alternatively be connected via a butt joint rather than being in overlapping connection. The reservoir 24 overlaps the distal end of the capture medium 32. These four components together form a single fluid path, and they cooperate to cause sample liquid to flow from the absorbent 12 along the release medium 30 and the capture medium 32 into the reservoir 24.

The invention is not limited by the precise nature of the capture site 34 and the corresponding control site 36, and in fact, the control site 36 may be entirely eliminated if desired. Generally, antibody or other affinity agent can be immobilized at the capture site 34 and the control site 36 using absorption, adsorption, or ionic or covalent coupling, in accordance with methods known per se. The capture medium 32 preferably is selected to bind the capture reagents without the need for chemical coupling. Nitrocellulose and nylon both permit non-chemical binding of the capture component and control reagent.

Disposed downstream of the capture medium 32 is the reservoir 24 comprising a relatively large mass of absorbent or superabsorbent material. The purpose of reservoir 24 is generally to ensure that a reasonably large amount of test liquid is drawn across the chromatographic medium. In certain embodiments, the sample absorbent 12 can be omitted, and the release medium 30 can itself act as the sample absorbent. Such embodiments of the assay materials are useful in performing dipstick assays.

As described above, the test device of the invention can generally be described as comprising a first portion and a second portion. The first portion of the test device comprises at least a labeled conjugate. The labeled conjugate comprises a binding member that is reactive with a first epitope of the analyte to be detected by the device. Such binding member can be any agent typically recognized in the art for such use and can particularly be any of the various materials as described herein. The conjugate further comprises a label component. Any label generally recognized in the art as being useful could be used according to the invention. In particular embodiments, the label specifically comprises colloidal gold, as more particularly described herein.

In embodiments wherein the test device comprises a biphasic substrate the first portion of the test device can refer to the release medium portion of the biphasic substrate.

As noted above, the release medium generally has two components disposed thereon: (i) a labeled conjugate comprising a specific binding protein (e.g., a monoclonal antibody reactive with a first epitope of the analyte), the protein being labeled with a visually detectable marker, such as colloidal gold particles; and (ii) a capturable conjugate comprising a binding protein (e.g., an antibody) and an affinity member (e.g., biotin), the capturable conjugate preferably being disposed downstream of the labeled conjugate. The biotinylated antibody is reactive with a second epitope of the analyte and is capable of forming a sandwich complex with the labeled antibody and the analyte.

Polyclonal antisera and monoclonal antibodies or fractions thereof having specific binding properties and high affinity for virtually any antigenic substance which are useful in the present invention as binding members and capture materials are known and commercially available, or can be produced from stable cell lines using well known cell fusion and screening techniques. The literature is replete with protocols for producing and immobilizing proteins. See, for example, Laboratory Techniques in Biochemistry and Molecular Biology, Tijssen, Vol. 15, Practice and Theory of Enzyme immunoassays, chapter 13, The Immobilization of Immunoreactants on Solid Phases, pp. 297 328, and the references cited therein.

Metal sols and other types of colored particles useful as marker substances in immunoassay procedures are also known per se. See, for example, U.S. Pat. No. 4,313,734. For details and engineering principles involved in the synthesis of colored particle conjugates see Horisberger, Evaluation of Colloidal Gold as a Cytochromic Marker for Transmission and Scanning Electron Microscopy, Biol. Cellulaire, 36, 253 258 (1979); Leuvering et al., Sol Particle Immunoassay, J. Immunoassay, 1 (1): 77 91 (1980), and Frens, Controlled Nucleation for the Regulation of the Particle Size in Monodisperse Gold Suspensions, Nature, Physical Science, 241: 20 22 (1973).

The present invention provides a test device having improved overall sensitivity. For example, in the case of a pregnancy test device, the invention provides for improved sensitivity by indicating the presence of hCG at a lower level than previously possible while still maintaining the test specificity. In one embodiment, this is achieved by increasing the intensity of color development at the test line. This particularly improves the overall readability of the product by the consumer.

Use of metal sols, such as colloidal gold, generally allows an individual to use a diagnostic device in light of a color-change brought about by the metal sol. For example, in home pregnancy devices, a consumer is able to visually read the test results due to the color provided by a gold colloid tagged anti-hCG antibody. Such known test devices typically use colloidal gold particles having a mean particle size that is relatively small in size, such as in the range from 40-47 nm.

As seen in the biphasic chromatographic substrate 18 of FIG. 3, the capture site 34 and the control site 36 are serially located on the substrate 18. The capture site and the control site are typically within the field of the window 16 (see FIG. 2A) and make up the test line and control line, respectively. The presence or absence of color at these lines is the indicator used to read the test result. As the test and control lines are not visible in the absence of the color provided by the gold colloid, increasing the visibility of the gold particle used in the test device causes an increase in color intensity at the test and control lines. Such increased color intensity directly corresponds to improved readability by the consumer.

In certain embodiments, the present invention achieves improved readability in a test device as described herein through use of colloidal gold particles having a larger mean particle size than previously used in such diagnostic devices. Generally, the particle sizes disclosed herein reference particle size prior to conjugation of the colloidal gold particle with a binding member as previously described. In preferred embodiments, the diagnostic test devices of the invention comprise colloidal gold particles having a mean particle size that is greater than about 50 nm. In further embodiments, the mean particle size of the colloidal gold particles is greater than about 52 nm, greater than about 55 nm, greater than about 57 nm, or greater than about 60 nm.

The visually observed color of colloidal gold particles is generally dependant upon the particle size. For example, particles up to about 100 nm in size exhibit an intense red color while particles greater than about 100 nm in size exhibit a somewhat more muted color. Thus, while it is possible according to the invention to use gold particles greater than about 100 nm in size, in preferred embodiments, the test device of the present invention preferentially uses gold particle sizes providing the red color.

The smaller particle size colloidal gold previously used provided the desirable red color, however, the color intensity was lacking and did not always provide a definitive color change that was easily recognizable by a consumer. It is only according to the present invention, however, that it has been discovered that by particularly using the larger particle size colloidal gold could the intensity of the characteristic red color be significantly increased. In fact, the use of the larger size particles provides an intense red color and provides for an accurate indication of the presence of analyte, even at very low levels. This correlates into early detection, which is highly desirable, particularly with assays, such as pregnancy tests. Accordingly, in further embodiments, the colloidal gold particles used in the invention have a mean particle size of from 50 nm to 100 nm, from 55 nm to 90 nm, from 55 nm to 85 nm, from 60 nm to 80 nm, from 60 nm to 75 nm, or from 65 nm to 75 nm.

Preferably, the gold particles used according to the present invention are substantially spherical in shape. However, other shapes could also be used. The gold particles are particularly characterized in that they are prepared to be monodisperse and have a narrow particle size distribution after preparation. The particles are greater than 95% monodisperse as determined by a Coulter N4 Particle Analyzer (Beckman Coulter, Fullerton, Calif.).

Production of gold particles for use in applications such as this is well known in the field and the particles may be prepared by any conventional process. The production of the larger gold particles builds off of this knowledge, but should be treated as a trade secret.

The results achieved by the present invention are particularly surprising in that a change in mean particle size of only a few nanometers corresponds to a significant increase in color intensity. In particular, when devices containing the larger gold particles of the present invention were tested against known devices using urine standards containing hCG, the test devices of the present invention including the larger gold particles consistently outperformed the known devices using the smaller gold particles. Specifically, the devices of the present invention exhibited an increase in color intensity of at least 25% when measured quantitatively.

Figure 6:
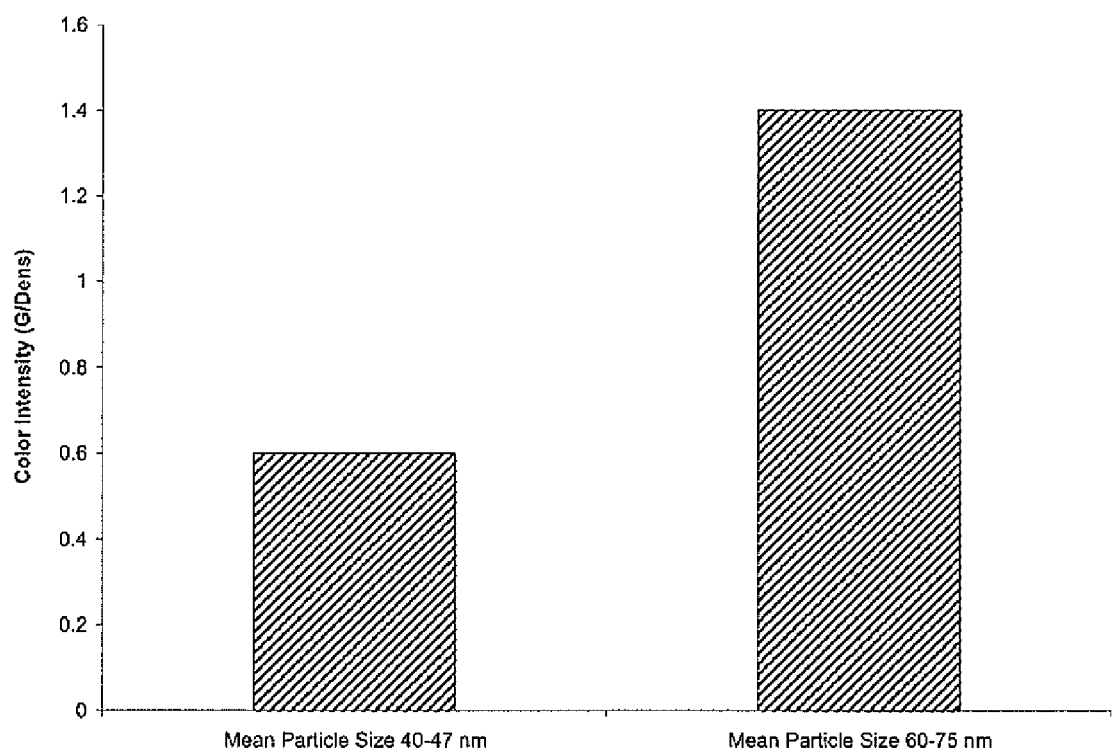
FIG. 6 is a chart illustrating the improved color intensity provided by certain embodiments of the invention incorporating colloidal gold particles having a mean particle size of 60-75 nm in comparison to the use of colloidal gold particles having a mean particle size of 40-47 nm.

The chart provided in FIG. 6 illustrates the improved readability provided by the use of gold particles having a larger mean particle size according to the invention. The test evaluated the color intensity at the test line of a device prepared using colloidal gold particles having a mean particle size of 40-47 nm and a device prepared using colloidal gold particles having a mean particle size of 60-75 nm. All other aspects of the device were identical. A sample comprising 12.5 mIU hCG/mL was added to the device and color was allowed to develop at the test lines. The devices were then evaluated using a Biodot test machine (Biodot Test Strip Reader (CCD Camera with image analysis software) Part Number TSR 3000) to quantitate the relative color intensity at the test lines. Other methods to quantitate relative color intensity are conventional, well known in the art, and may also be employed. The G/Dens value for the smaller gold particles was about 0.6, while the G/Dens value for the inventive larger gold particles was about 1.4.

The device according to the invention using the larger size colloidal gold particles generally provides at least a 25% increase in color intensity over the color intensity of devices using the smaller size gold particles. As seen in FIG. 6, the use of gold particles having a larger mean particle size according to the invention provided approximately a 40% increase in color intensity over the use of smaller gold particles when detecting 12.5 mIU hCG/mL of sample.

The improvements provided by the use of the larger colloidal gold particles allows for increased accuracy and efficiency in a variety of test procedures. In embodiments incorporating a single phase medium, the larger particle size colloidal gold can effectively improve the readability of the test. Thus, the present invention can be useful in increasing performance in a variety of known diagnostic test devices.

In embodiments incorporating a biphasic substrate, the release medium provides the labeled conjugate (which can include the larger colloidal gold particles described above) and a capturable conjugate. Preferably, the capturable conjugate comprises a capturable component and an antibody that is reactive with the analyte in the test sample, such as hCG. Disposed on the capture medium is a capture site for capturing and immobilizing the complex. The capture site has immobilized thereon a capture component which has a high affinity for the capturable component. Presently, pregnancy tests based on a biphasic substrate use biotin chemically attached to the antibody as the capturable conjugate and streptavidin as the capture component. Such tests rely on the strong affinity between streptavidin and biotin in order to generate a positive result at the test line. Accordingly, in the presence of hCG, the "sandwich" formed between the gold-hCG-biotin complex are captured at the test line by the binding of the monomeric streptavidin molecules to the biotin portion of the "sandwich".

While the biotin-streptavidin interaction is strong, the overall signal at the test line is limited by the binding between the streptavidin and the nitrocellulose. Previously known test devices utilizing streptavidin as a capture component use monomeric streptavidin, but monomeric streptavidin is plagued by weak binding to the nitrocellulose substrate. This weak binding of the monomeric streptavidin allows a portion of the streptavidin bound to the nitrocellulose to wash away as the test fluid wicks up the substrate. The ease of the streptavidin being dislodged from the substrate decreases the overall efficiency of the analyte capture. The present invention overcomes this deficiency by increasing the strength of the binding between the streptavidin and the substrate. Thus, a stronger signal at the capture site is achieved by better retention of the streptavidin.

In certain embodiments of the invention, the test device comprises polymerized streptavidin. Polymerized streptavidin is particularly useful because it maintains the high affinity for biotin that is characteristic of monomeric streptavidin, but the polymeric nature of the larger streptavidin polymer causes the polymerized streptavidin to become more efficiently immobilized to the test device substrate, such as a nitrocellulose membrane. The stronger immobilization of the polymerized streptavidin leads to a more efficient capture of the capturable "sandwich" component (e.g., a gold-hCG-biotin complex). Thus, a test device according to the invention comprising polymerized streptavidin at the capture site provides increased signaling of detected analyte because the polymerized streptavidin is not dislodged from the substrate by wicking action of the liquid test sample across the substrate, such as is a problem with monomeric streptavidin.

Monomeric streptavidin typically has an average size in the range of about 53 kDa. Polymerized streptavidin according to the invention has an average size that is distinguishably larger. As further described below, the polymerized streptavidin used in the invention can comprise a mixture of polymerized streptavidin species. Preferably, the polymerized streptavidin mixture comprises greater that 50% by weight streptavidin species having a size of at least about 100 kDa. In further embodiments, the polymerized streptavidin comprises greater than 55% by weight, greater than 60% by weight, greater than 70% by weight, or greater than 80% by weight streptavidin species having a size of at least about 100 kDa.

The polymerized streptavidin used according to the invention can be prepared from monomeric streptavidin using any method recognized as useful in the art. In one embodiment, polymerized streptavidin is prepared by crosslinking monomeric streptavidin via incubation with an aldehyde (such as formaldehyde, glutaraldehyde, or the like).

The methods for attaching the streptavidin, either monomeric or polymerized, to the substrate can also vary according to the invention. For example, in certain embodiments, the streptavidin can be attached directly to the substrate. In other embodiments, the streptavidin can be indirectly attached to the substrate, such as through a natural or synthetic intermediate material. In one specific embodiment, the streptavidin can be attached to the substrate via a particulate material, such as latex beads. For example, the streptavidin can be attached to latex beads via passive adsorption or chemical coupling, and the latex-bound streptavidin can be dispensed onto the substrate by bonding the latex beads thereto. Preferentially, such latex beads have sizes in the range of about 0.1 μm to about 0.5 μm, more preferably about 0.1 μm to about 0.3 μm.

In yet another embodiment, the streptavidin can be conjugated to an intermediate protein, the intermediate protein being bound to the substrate. Non-limiting examples of materials useful as an intermediate protein for attaching streptavidin to a substrate include immunoglobulins and bovine serum albumin (BSA).

Figure 7:
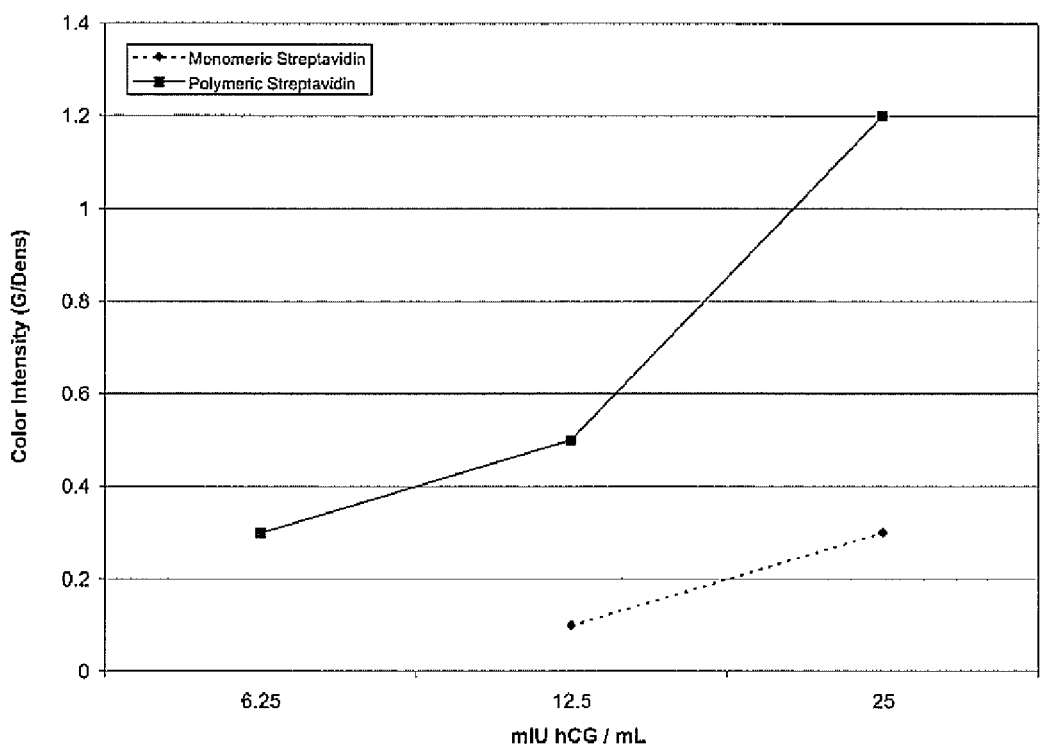
FIG. 7 is a chart illustrating the improved color intensity provided by certain embodiments of the invention incorporating polymeric streptavidin in comparison to the use of monomeric streptavidin.

When tested against urine standards containing varying levels of hCG, devices according to the invention comprising polymerized streptavidin at the test line consistently outperform devices containing monomeric streptavidin. This improved performance of the present test device is illustrated in FIG. 7, which graphically shows the benefits of polymerized streptavidin over monomeric streptavidin. Specifically, test devices were prepared using either monomeric streptavidin or polymeric streptavidin, all other aspects of the devices being identical (including the use of colloidal gold particles having the smaller size typically used in the art). The devices were evaluated using urine standards containing 6.25 mIU hCG per mL of sample, 12.5 mIU hCG per mL of sample, and 25 mIU hCG per mL of sample. Color development at the test line was quantitated using a Biodot test apparatus five minutes after application of the urine sample. As seen in FIG. 7, the inventive device comprising polymerized streptavidin at the test line consistently exhibited a 2-3 fold increase in color intensity at the test line when compared to parallel devices using monomeric streptavidin at the test line.

The polymerized streptavidin not only provides an increase in color intensity but also allows for detection of analyte at a lower sample concentration than possible using monomeric streptavidin. As shown in FIG. 7, urine samples containing as little as 6.25 mIU hCG per mL of sample were detectable (exhibited quantifiable color formation) while no color formation was detectable at this low concentration using monomeric streptavidin on the test line.

The streptavidin used in the preparation of test devices according to the invention preferably comprises a streptavidin solution that can be applied to the test device, thereby immobilizing streptavidin on the substrate. The streptavidin in the solution can comprise a number of polymerized forms, such as dimeric, trimeric, tetrameric, or the like. While monomeric streptavidin can be present in the solution, the solution preferably comprises a majority of polymerized streptavidin, the total content of any monomeric streptavidin in the solution comprising only a minority of the total content of the solution. In specific embodiments, the streptavidin solution comprises polymerized streptavidin in an amount such that the polymerized streptavidin comprises at least 50% by weight of the streptavidin solution. Preferably, the solution comprises at least about 55% by weight, at least about 60% by weight, at least about 75% by weight, or at least about 90% by weight of polymerized streptavidin.

In particular embodiments, the immunoassay device of the present invention is designed to detect human pregnancy. In this embodiment, the labeled binding member is preferably a monoclonal antibody (MAb) against human chorionic gonadotropin (hCG) labeled with a visually detectable label, such as colloidal gold. For this purpose, MAb designated 11D6 (available from Church & Dwight Co., Inc.) is particularly preferred. Anti-hCG antibodies (preferably monoclonal antibodies) labeled with biotin can be used for the capturable complex. For this purpose, monoclonal antibody designated CCF01 (available from Scripps Laboratory) is particularly preferred. Methods for conjugating biotin to antibodies are known in the art. In a preferred embodiment, the capture site comprises streptavidin, which has a high affinity for biotin. A control site preferably is located downstream of the capture site and can have immobilized thereon goat anti-mouse IgG specific for the anti-hCG antibody (available from Scantibodies Laboratory).

The test devices of the present invention are particularly useful in that they allow for the detection of hCG at surprisingly low levels. This is beneficial in that the ability to detect low levels of hCG directly correlates to the ability to detect pregnancy soon after conception. Specifically, the devices of the present invention are able to detect pregnancy sooner after conception than possible using devices previously provided in the art. In specific embodiments, the test devices of the invention are capable of detecting hCG in a sample in concentrations as low as 6.25 mIU hCG/mL. In other embodiments, the test devices of the invention are capable of detecting hCG in a sample in concentrations as low as 3.15 mIU hCG/mL.

In light of the surprising advantages described above in relation to the separate use of relatively large colloidal gold particles and polymerized streptavidin, in specific embodiments, the present invention provides an improved pregnancy test kit that is particularly advantageous over known test kits. The particular advantages arise from the combination of the improvements described herein. The surprising effects of the combination of the improvements are further described in the Examples.

In one specific embodiment, the invention provides a human pregnancy test device that detects the presence of hCG in a test sample, such as urine. The device is preferentially useful for the measurement of hCG in urine as early as five days before the beginning of an expected menses or six days before the day of a missed menses. This represents a significant improvement over the known art wherein hCG cannot be detected as early as five days before the beginning of an expected menses.

Pregnancy test devices according to the invention provide improved test results without sacrificing clinical accuracy (i.e., the ability to correctly determine the test condition, such as pregnant versus not pregnant). As illustrated below in Example 3, pregnancy test devices according to the invention provide extremely high clinical accuracy in addition to improved readability (which improves analytical accuracy or the ability of a consumer to interpret test results) and earlier diagnosis.

Preferably, the test devices of the invention are capable of providing a defined level of clinical accuracy. Such accuracy can be related to a specific time at which the test condition can be detected. For example, in the case of a pregnancy test, the device of the invention can be described in terms of ability to determine pregnancy a specified number of days prior to the expected onset of menses. In specific embodiments, the inventive test device can determine pregnancy with a clinical accuracy of at least 98% up to three days prior to the expected onset of menses.

In another embodiment the present immunoassay device is designed to predict human ovulation. In this embodiment, the labeled binding member preferably comprises monoclonal antibody, such as clone number 057-10036 (available from Church & Dwight Co., Inc.), which is specific for leuteinizing hormone (LH), labeled with a label such as colloidal gold. The capturable complex preferably comprises biotinylated LH-specific monoclonal antibody designated 5304 (available from Biospecific, Emeriville, Calif.). The capture site preferably comprises streptavidin and the control site comprises goat anti-mouse IgG specific for the labeled MAb.

In yet another embodiment, the device may be adapted to detect infectious agents, such as streptococcus. In this embodiment, the labeled binding member is preferably a polyclonal antibody (such as rabbit polyclonal antibody) specific for streptococcus labeled with colloidal gold or other direct marker. The capturable complex is preferentially the same polyclonal antibody conjugated to biotin, and the capture and control components can comprise streptavidin and goat anti-rabbit IgG.

In further embodiments, the invention provides various methods for detecting the presence of an analyte (such as hCG) in a liquid sample. The methods of the invention generally comprise the use of a test device as described herein. Typically, the methods of the invention comprise adding a liquid sample to a first portion of an inventive device, allowing the liquid sample to flow across a substrate in the test device (e.g., a biphasic substrate comprising a release medium and a capture medium), and determining the presence of the analyte in the liquid sample by visual inspection. Preferentially, the presence of the analyte is indicated by the presence of color development caused by accumulation of a label component at a capture site.

EXPERIMENTAL

The present invention will now be described with specific reference to various examples. The following examples are not intended to be limiting of the invention and are rather provided as exemplary embodiments.

Example 1

Readability of Pregnancy Test Kit

Three specific embodiments of a pregnancy test device according to the invention were prepared. The inventive pregnancy tests were prepared using a biphasic substrate as generally described above but incorporating the inventive aspects described herein. Specifically, the inventive pregnancy test devices used the large colloidal gold particles and polymerized streptavidin described herein, and the release medium and capture medium were non-overlapping (i.e., connected via a butt joint). In inventive strip 1, the large particle colloidal gold (i.e., mean particle size of 60-75 nm) was coated on the test line at an optical density of 30 when measured at 533 nm (i.e., 30 $OD_{533}$). For inventive strips 2 and 3, the large particle colloidal gold was coated at 25 $OD_{533}$ and 20 $OD_{533}$, respectively. Comparative strips 1-3 were prepared using monomeric streptavidin, small particle gold (i.e., mean particle size of 40-47 nm) coated at 30 $OD_{533}$, 25 $OD_{533}$, and 20 $OD_{533}$, and overlapping release medium and capture medium. Strip compositions are summarized below in Table 1.

TABLE 1

| Strip ID | Composition |
| --- | --- |
| Inventive Strip 1 | 30 $OD_{533}$ large particle colloidal gold probe/polymeric streptavidin/non-overlapping biphasic substrate |
| Inventive Strip 2 | 25 $OD_{533}$ large particle colloidal gold probe/polymeric streptavidin/non-overlapping biphasic substrate |
| Inventive Strip 3 | 20 $OD_{533}$ large particle colloidal gold probe/polymeric streptavidin/non-overlapping biphasic substrate |
| Comparative Strip 1 | 30 $OD_{533}$ small particle colloidal gold probe/monomeric streptavidin/overlapping biphasic substrate |
| Comparative Strip 1 | 25 $OD_{533}$ small particle colloidal gold probe/monomeric streptavidin/overlapping biphasic substrate |
| Comparative Strip 1 | 20 $OD_{533}$ small particle colloidal gold probe/monomeric streptavidin/overlapping biphasic substrate |

Figure 8:
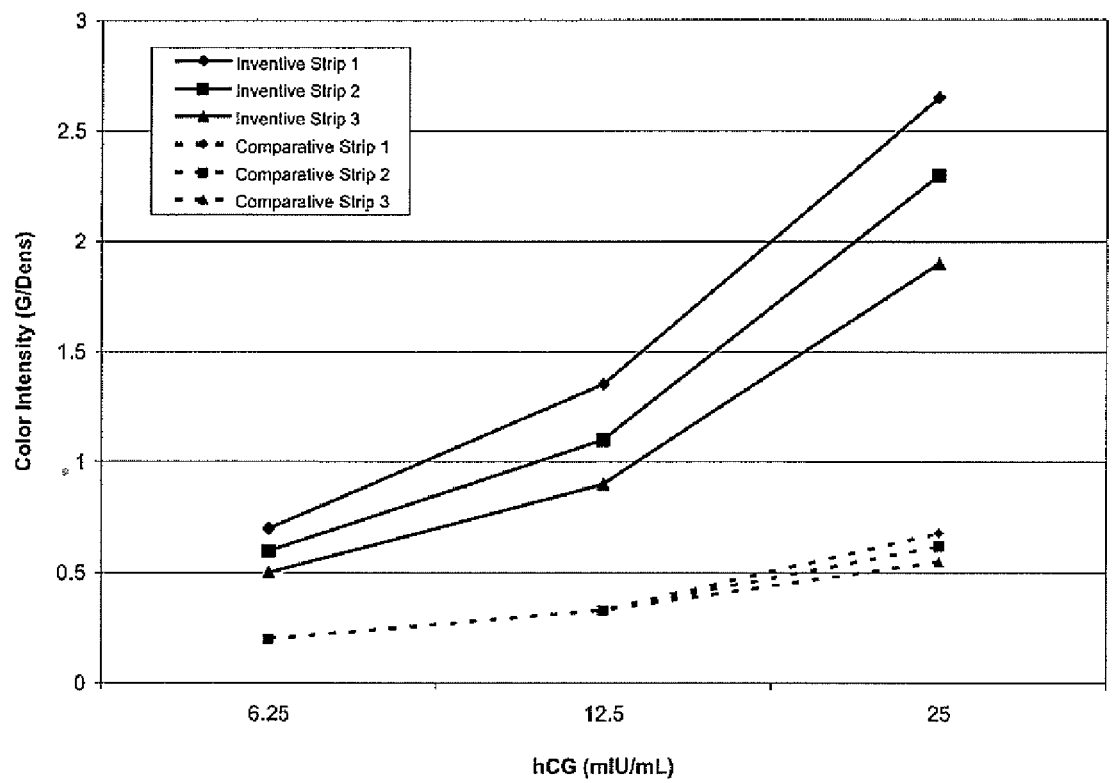
FIG. 8 is a chart illustrating the improved color intensity provided by certain embodiments of the invention incorporating large particle colloidal gold and polymeric streptavidin in comparison to the use of small particle colloidal gold and monomeric streptavidin.

When tested against urine standards containing varying levels of hCG, the pregnancy test kits incorporating the inventive strips according to the invention consistently outperformed the comparative pregnancy test kits using known technology. These results are graphically illustrated in FIG. 8. Specifically, each test strip was tested using samples with hCG concentrations of 6.25, 12.5, or 25 mIU hCG/mL and evaluated for color intensity (G/Dens) using a Biodot test apparatus. The inventive combination of the larger more visible gold probe with increased efficiency of capture at the test line associated with the polymerized streptavidin resulted in devices that provide a greater color intensity at the test line (e.g., greater than a 3-fold increase). The inclusion of the non-overlapping biphasic medium had no positive or negative effect on overall performance. While it may be beneficial from a manufacturing standpoint, it is considered a non-critical component for the benefits associated with large gold and polymerized streptavidin.

Example 2

Capture Efficiency of Polymeric Streptavidin

Figure 9:
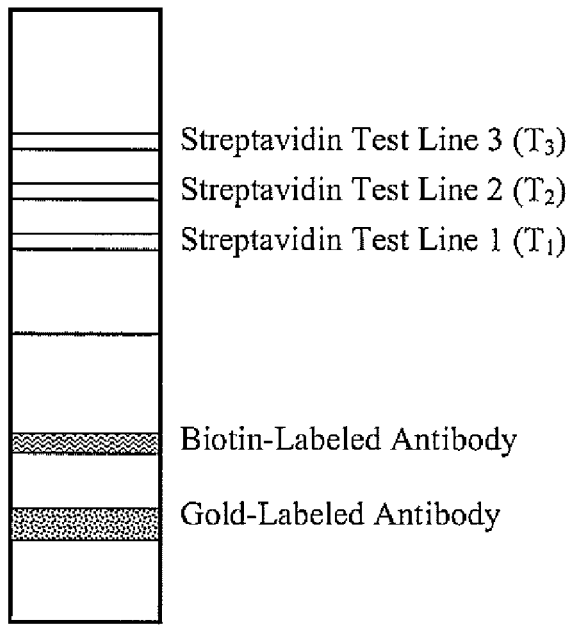
FIG. 9 is a schematic top view of a biphasic test strip for use in evaluating the capture efficiency of polymeric streptavidin in comparison to monomeric streptavidin.

The ability of polymerized streptavidin used as a capture component to generate increased color development was evaluated. A biphasic test strip was used and the release medium was striped with OD 25 large particle gold probe according to the invention. A stripe of biotin was placed on the release medium downstream of the gold probe stripe. The capture medium was striped with three test lines ($T_1$, $T_2$, and $T_3$) of polymeric streptavidin or three test lines ($T_1$, $T_2$, and $T_3$) of monomeric streptavidin. The test strip is illustrated in FIG. 9. The monomeric streptavidin stripes were applied using a solution of 1.5 mg/mL of monomeric streptavidin. Likewise, the polymeric streptavidin stripes were applied using a solution of 1.5 mg/mL of polymeric streptavidin.

Replicates of 5 samples were tested with urine standards containing 25, 50, and 100 mIU hCG/mL of sample. All test stripes were read on a Biodot Test Strip Reader (available from Biodot, Inc., Irvine, Calif.) 5 minutes after application of the urine standard solution to quantitate the color development at each individual test line. Result data is summarized below in Table 2.

TABLE 2

| hCG Concentration (mIU/mL) | Monomeric Streptavidin Test Lines Color Intensity (G/Dens) | | | Polymeric Streptavidin Test Lines Color Intensity (G/Dens) | | |
|---|---|---|---|---|---|---|
| | $T_1$ | $T_2$ | $T_3$ | $T_1$ | $T_2$ | $T_3$ |
| 25 | 1.08 | 0.97 | 0.37 | 3.34 | 0.82 | 0.24 |
| 50 | 2.18 | 2.05 | 0.66 | 6.46 | 1.38 | 0.32 |
| 100 | 4.61 | 3.42 | 1.14 | 9.36 | 1.65 | 0.44 |

Figure 10:
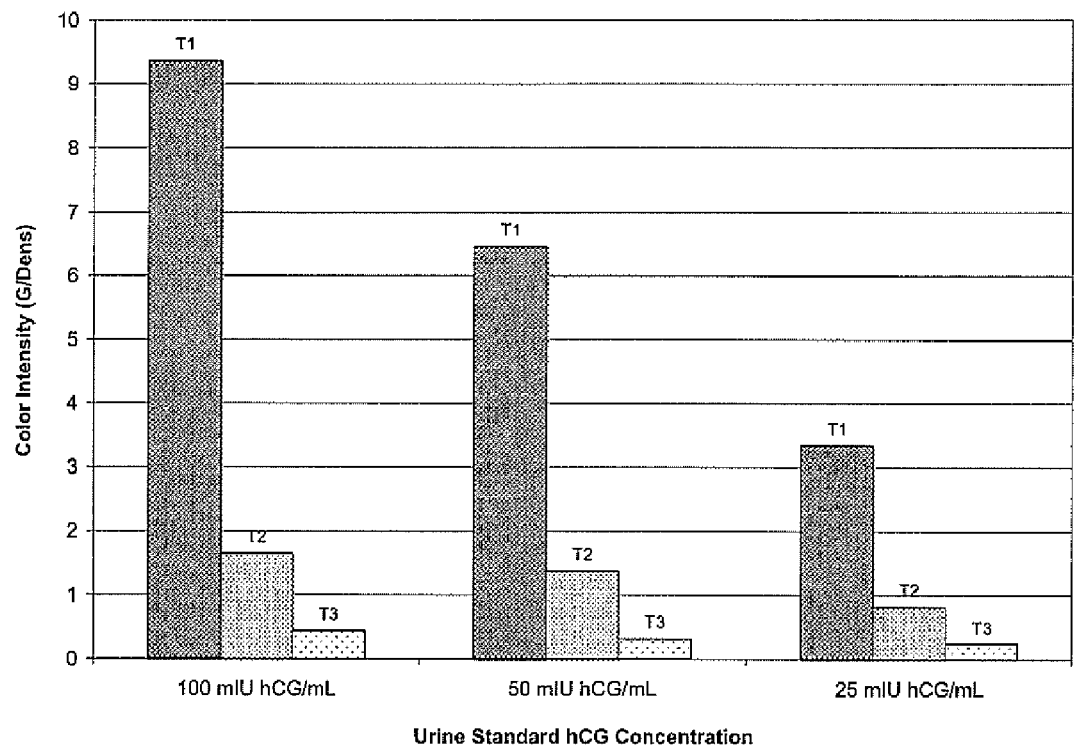
FIG. 10 is a chart illustrating the improved ability of a test device according to the invention to collect and retain an analyte complex on a test strip having a capture site striped with polymeric streptavidin.

Comparison of the color intensity at the initial test line ($T_1$) for the monomeric streptavidin and the polymeric streptavidin as provided in Table 2 indicates, as previously noted, that the use of polymerized streptavidin provides approximately three times greater color development at the test line when compared to monomeric streptavidin. These test results are graphically illustrated in FIG. 10 (illustrating the polymeric streptavidin test results) and FIG. 11 (illustrating the monomeric streptavidin test results).

The results observed at the additional test lines ($T_2$ and $T_3$) indicate that polymeric streptavidin is more efficient at capturing the hCG analyte complex as it flows down the biphasic material. Specifically, as shown in Table 2 and FIG. 10, there is high binding at the initial test line ($T_1$) and comparatively low binding at the additional downstream test lines ($T_2$ and $T_3$). The low level of binding observed at $T_2$ and $T_3$ indicates that when polymeric streptavidin is used, the hCG analyte complex is efficiently captured, and retained, at the initial test line. Thus, very little complex remains in the test solution to move downstream and bind at $T_2$ or $T_3$. Moreover, very little complex is detached from $T_1$ to move downstream.

Figure 11:
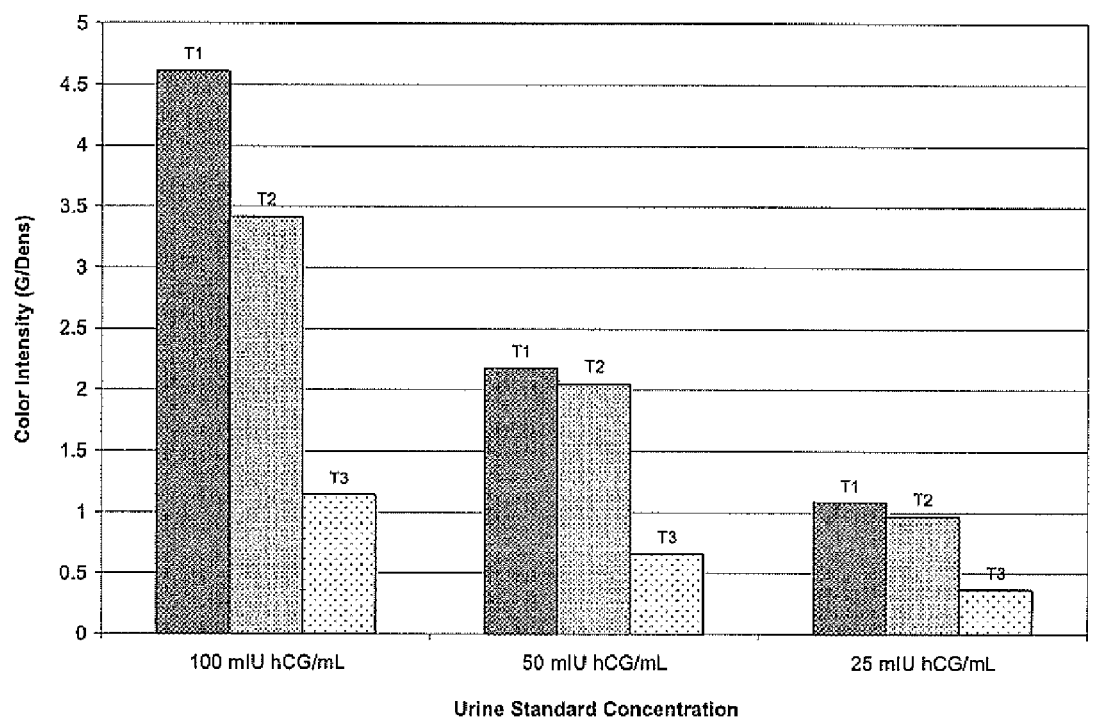
FIG. 11 is a chart illustrating the inability of known test devices to collect and retain an analyte complex on a test strip having a capture site striped with monomeric streptavidin.

The monomeric streptavidin does not provide such beneficial properties. First, the monomeric streptavidin is not as efficient at capturing the hCG analyte complex. As seen in Table 2 and FIG. 11, the initial test line shows much less binding than the initial test line ($T_1$) in FIG. 10. Further, in comparison to $T_1$, the binding observed downstream at $T_2$ and $T_3$ in FIG. 11 is much higher than observed in FIG. 10. In fact, at 50 mIU hCG/mL and 25 mIU hCG/mL, the amount of analyte complex captured at $T_2$ was almost identical to the amount captured and retained at $T_1$ when using the monomeric streptavidin. This high level of binding at the downstream test lines ($T_2$ and $T_3$) indicates that when monomeric streptavidin is used, a greater proportion of the analyte complex flows past the initial test without binding thereto and is available for binding downstream. Moreover, bound complex is more easily detached using the monomeric streptavidin.

Example 3

Pregnancy Test Clinical Accuracy

A pregnancy test device according to the invention was evaluated to determine the accuracy of the device. The inventive pregnancy tests were prepared using a biphasic substrate as generally described above but incorporating the inventive aspects described herein. Specifically, the inventive pregnancy test devices used the large colloidal gold particles (i.e., mean particle size of 60-75 nm) and polymerized streptavidin described herein. A total of 153 urine samples were tested, each sample being known to include hCG (i.e., indicating pregnant) or not include hCG (i.e., indicating not pregnant). Test results are summarized below in Table 3.

TABLE 3

| Urine Sample | Number | Number Determined by Inventive Device | Accuracy |
|---|---|---|---|
| Non-Pregnant | 103 | 103 | 100% |
| Pregnant | 50 | 50 | 100% |
| Total | 153 | 153 | 100% |

Example 4

Test Device Sensitivity for hCG

The analytical sensitivity of a pregnancy test device according to the invention was evaluated using a negative urine pool (NUP) that was spiked with 8, 10, or 12 mIU hCG/mL of sample. The NUP was comprises of urine samples from a minimum of 20 non-pregnant individual donors. The samples were evaluated with 25 identical test devices according to the invention. The inventive pregnancy tests were prepared using a biphasic substrate as generally described above but incorporating the inventive aspects described herein. Specifically, the inventive pregnancy test devices used the large colloidal gold particles (i.e., mean particle size of 60-75 nm) and polymerized streptavidin described herein. Samples including hCG were tested to ensure a positive pregnancy result by the inventive device. The results are provided below in Table 4.

TABLE 4

| 8 mIU hCG/mL | 10 mIU hCG/mL | 12 mIU hCG/mL |
|---|---|---|
| 25/25 Positive | 25/25 Positive | 25/25 Positive |

To confirm the results provided above, five test devices according to the invention were each tested in urine standards prepared to have varying levels of hCG present therein (40 total test devices). Samples including hCG were tested to ensure a positive pregnancy result by the inventive device and samples having no hCG present therein were tested to ensure a negative pregnancy result by the inventive device. The results are provided below in Table 5. As seen therein, all samples tested at all hCG concentrations exhibited the expected negative or positive test results.

TABLE 5

| 0 mIU hCG per mL | 3.2 mIU hCG per mL | 6.3 mIU hCG per mL | 10 mIU hCG per mL | 12.5 mIU hCG per mL | 18.8 mIU hCG per mL | 25 mIU hCG per mL | 50 mIU hCG per mL |
|---|---|---|---|---|---|---|---|
| 5/5 Negative | 5/5 Positive | 5/5 Positive | 5/5 Positive | 5/5 Positive | 5/5 Positive | 5/5 Positive | 5/5 Positive |

Example 5

Test Device Sensitivity for H-hCG

Test devices according to the invention were evaluated to determine sensitivity to hyperglycosylated hCG (H-hCG), the principal hCG-related molecule present in early pregnancy. Five test devices were each tested in urine standards prepared to have varying levels of H-hCG present therein (40 total test devices). The inventive pregnancy tests were prepared using a biphasic substrate as generally described above but incorporating the inventive aspects described herein. Specifically, the inventive pregnancy test devices used the large colloidal gold particles (i.e., mean particle size of 60-75 nm) and polymerized streptavidin described herein. Samples including H-hCG were tested to ensure a positive pregnancy result by the inventive device and samples having no H-hCG present therein were tested to ensure a negative pregnancy result by the inventive device. The results are provided below in table 6. As seen therein, all samples tested at all hCG concentrations exhibited the expected negative or positive test results.

TABLE 6

| 0 mIU H-hCG per mL | 3.2 mIU H-hCG per mL | 6.3 mIU H-hCG per mL | 10 mIU H-hCG per mL | 12.5 mIU H-hCG per mL | 18.8 mIU H-hCG per mL | 25 mIU H-hCG per mL | 50 mIU H-hCG per mL |
|---|---|---|---|---|---|---|---|
| 5/5 Negative | 5/5 Positive | 5/5 Positive | 5/5 Positive | 5/5 Positive | 5/5 Positive | 5/5 Positive | 5/5 Positive |

Example 6

Detection of hCG in Early Pregnancy Clinical Samples

Early pregnancy studies were performed with approximately 575 samples from a total of 52 individual conceptive cycles. The testing segment in each conceptive cycle commences with the two consecutive negative samples (hCG values<1 mIU/mL) followed by the first sample demonstrating a rise in hCG (>1 mIU/mL) collected around the expected time of implantation (approximately 5-7 days post-ovulation), and the testing segment ended with the sample collected 3 days after the expected menstrual period (EMP). Each sample was tested using an inventive pregnancy test according to the invention, all of which were prepared using a biphasic substrate as generally described above but incorporating the inventive aspects described herein. Specifically, the inventive pregnancy test devices used the large colloidal gold particles (i.e., mean particle size of 60-75 nm) and polymerized streptavidin described herein.

The test results are provided below in Table 7 and Table 8. The tests are categorized according to the day of the test relative to the EMP (e.g., EMP-8 means the day eight days prior to the expected onset of the menstrual period, EMP alone means the day of expected onset, and EMP+1 means the number of days of missed menstrual period). For reference, the day relative to ovulation (OV) is also provided (e.g., OV+7 means the day 7 days after ovulation occurred). The number of cycles wherein the inventive test device provided a positive pregnancy test result is provided relative to the total number of tests carried out for the given cycle. The table further provides the cumulative percentage of cycles testing positive for hCG.

TABLE 7

| Day Relative to Expected Menstrual Period | EMP – 8 | EMP – 7 | EMP – 6 | EMP – 5 | EMP – 4 |
|---|---|---|---|---|---|
| Day Relative to Ovulation | OV + 7 | OV + 8 | OV + 9 | OV + 10 | OV + 11 |
| No. of Cycles Positive for hCG | 1/32 | 14/44 | 26/49 | 41/50 | 45/50 |

TABLE 7-continued

| | | | | | |
|---|---|---|---|---|---|
| Cumulative % of Cycles Positive for hCG | 3% | 27% | 53% | 82% | 90% |

TABLE 8

| | | | | | |
|---|---|---|---|---|---|
| Day Relative to Expected Menstrual Period | EMP − 3 | EMP − 2 | EMP − 1 | EMP | EMP + 1 |
| Day Relative to Ovulation | OV + 12 | OV + 13 | OV + 14 | OV + 15 | OV + 16 |
| No. of Cycles Positive for hCG | 44/45 | 48/48 | 49/49 | 47/47 | 50/50 |
| Cumulative % of Cycles Positive for hCG | 98% | 100% | 100% | 100% | 100% |

Example 7

Consumer Evaluation of Pregnancy Test Results

The ability of consumers to perform and interpret test results using a pregnancy test device according to the invention was evaluated. In the study, 104 women between the ages of 18 and 45 years, untrained in laboratory testing, participated. Each subject was asked to interpret the results of a test conducted using a device according to the invention. The devices were prepared using a biphasic substrate as generally described above but incorporating the inventive aspects described herein. Specifically, the inventive pregnancy test devices used the large colloidal gold particles (i.e., mean particle size of 60-75 nm) and polymerized streptavidin described herein. Each device evaluated by a test subject was pre-assayed with urine standards containing 0, 8, 10, or 12 mIU/mL of hCG.

The subject interpreted the result according to the package insert instructions provided with no help from the study monitor. Overall, six results were interpreted incorrectly, 3 pre-assayed with 8 mIU hCG and 3 pre-assayed with 10 mIU hCG/mL. No incorrect interpretations were made for test devices pre-assayed with no hCG or 12 mIU hCG/mL. The test results are provided below in Table 9.

TABLE 9

| Sample | Number Evaluated | Number of Correct Consumer Interpretations | Accuracy |
|---|---|---|---|
| 0 mIU hCG/mL | 104 | 104 | 100% |
| 8 mIU hCG/mL | 104 | 101 | 97% |
| 10 mIU hCG/mL | 104 | 101 | 97% |
| 12 mIU hCG/mL | 104 | 104 | 100% |
| Total | 416 | 410 | 98.6% |

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A device for detecting an analyte in a liquid sample deposited on a first portion of the device for transport to a second portion of the device that is in fluid contact with the first portion, wherein the device comprises:
   A) in the first portion thereof, a labeled conjugate comprising a binding member reactive with a first epitope of the analyte and a label comprising colloidal gold particles having a mean particle size of at least about 50 nm prior to formation of the labeled conjugate; and
   B) in the second portion thereof, a capture component that is directly or indirectly reactive with a second epitope of the analyte.

2. The device of claim 1, wherein the colloidal gold particles have a mean particle size of about 50 nm to about 100 nm.

3. The device of claim 1, wherein the colloidal gold particles have a mean particle size of about 55 nm to about 85 nm.

4. The device of claim 1, wherein the colloidal gold particles have a mean particle size of about 60 nm to about 80 nm.

5. The device of claim 1, wherein the colloidal gold particles have a mean particle size of about 60 nm to about 75 nm.

6. The device of claim 1, wherein the capture component is directly reactive with a second epitope of the analyte.

7. The device of claim 1, wherein the capture component is indirectly reactive with a second epitope of the analyte.

8. A method for determining the presence of an analyte in a liquid sample comprising:
   A) providing an analyte detection device comprising a substrate with a first portion comprising colloidal gold having a mean particle size of at least about 50 nm releasably immobilized thereon and a second portion in fluid communication with the first portion and comprising a capture component immobilized thereon;
   B) adding a liquid sample to the first portion of the device;
   C) allowing the liquid sample to flow across the first portion and the second portion of the substrate; and
   D) determining the presence of the analyte in the liquid sample by visual inspection of the second portion of the substrate, wherein the presence of the analyte is indicated by the presence of color development in the area wherein the capture component is immobilized caused by accumulation of the colloidal gold.

9. The method of claim 8, wherein the colloidal gold particles have a mean particle size of about 50 nm to about 100 nm.

10. The method of claim 8, wherein the colloidal gold particles have a mean particle size of about 55 nm to about 85 nm.

11. The method of claim 8, wherein the colloidal gold has a mean particle size of about 60 nm to about 80 nm.

12. The method of claim 8, wherein the colloidal gold particles have a mean particle size of about 60 nm to about 75 nm.

13. The method of claim 8, wherein the capture component comprises polymerized streptavidin.

14. The method of claim 13, wherein greater than 50% by weight of the polymerized streptavidin is at least about 100 kDa in size.

15. The method of claim 13, wherein the capture component is immobilized to the second portion through direct attachment of the polymerized streptavidin to the second portion.

16. The method of claim 13, wherein the capture component is immobilized to the second portion through indirect attachment of the polymerized streptavidin to the second portion.

17. The method of claim 16, wherein the indirect attachment is through an intermediate material selected from the group consisting of latex beads, immunoglobulins, bovine serum albumin, and combinations thereof.

18. The method of claim 8, wherein the color intensity caused by accumulation of the colloidal gold, when measured on a Biodot test apparatus, is at least 25% greater than the color intensity under the same conditions caused by accumulation of colloidal gold having a mean particle size of less than 50 nm.

* * * * *